(12) United States Patent
Beck et al.

(10) Patent No.: US 11,250,356 B2
(45) Date of Patent: Feb. 15, 2022

(54) METHOD AND SYSTEM FOR APPORTIONING TASKS TO PERSONS IN ENVIRONMENT

(71) Applicant: PANASONIC INTELLECTUAL PROPERTY MANAGEMENT CO., LTD., Osaka (JP)

(72) Inventors: Ariel Beck, Singapore (SG); Vasileios Vonikakis, Singapore (SG); Khai Jun Kek, Batu Pahat (SG); Chandra Suwandi Wijaya, Singapore (SG)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 69 days.

(21) Appl. No.: 16/366,963

(22) Filed: Mar. 27, 2019

(65) Prior Publication Data
US 2020/0311632 A1 Oct. 1, 2020

(51) Int. Cl.
*G06Q 10/00* (2012.01)
*G06Q 10/06* (2012.01)
*G01D 9/00* (2006.01)

(52) U.S. Cl.
CPC ....... *G06Q 10/06311* (2013.01); *G01D 9/005* (2013.01); *G06Q 10/06* (2013.01); *G06Q 10/063* (2013.01)

(58) Field of Classification Search
CPC ............. G06Q 10/06311; G06Q 10/06; G06Q 10/063; G01D 9/005
See application file for complete search history.

(56) References Cited

U.S. PATENT DOCUMENTS

| | | | |
|---|---|---|---|
| 9,179,847 B2 * | 11/2015 | Eggenberger | G09B 19/00 |
| 2002/0065700 A1 | 5/2002 | Powell et al. | |
| 2009/0006164 A1 | 1/2009 | Kaiser et al. | |
| 2017/0169382 A1 * | 6/2017 | Thapliyal | G06Q 10/1093 |
| 2017/0200112 A1 * | 7/2017 | Liu | G06Q 10/063114 |
| 2017/0216674 A1 * | 8/2017 | Nakai | G16H 20/30 |
| 2018/0032944 A1 * | 2/2018 | Sarvana | G06Q 10/063114 |
| 2018/0330302 A1 * | 11/2018 | Peterson | G10L 25/66 |
| 2020/0027369 A1 * | 1/2020 | Horita | G09B 19/00 |
| 2020/0035337 A1 * | 1/2020 | Sohne | G08B 21/182 |

(Continued)

OTHER PUBLICATIONS

Posada-Quintero HF, Bolkhovsky JB. Machine Learning models for the Identification of Cognitive Tasks using Autonomic Reactions from Heart Rate Variability and Electrodermal Activity. Behav Sci (Basel). 2019;9(4):45. (Year: 2019).*

(Continued)

*Primary Examiner* — Rutao Wu
*Assistant Examiner* — Tyrone E Singletary
(74) *Attorney, Agent, or Firm* — McDermott Will and Emery LLP

(57) ABSTRACT

The present disclosure relates to a method and system for apportioning tasks to person in an environment. The method comprises capturing a first-value indicating a sympathetic-nerve based activity and a second-value indicating a parasympathetic-nerve based activity for at least one person operating in an environment. Thereafter, a quantitative-relation is determined between the first and second values. At-least one task is assigned for execution by said person within the environment based on such quantitative relation.

6 Claims, 10 Drawing Sheets

(56) References Cited

U.S. PATENT DOCUMENTS

2020/0268299 A1* 8/2020 Kobayashi ............ A61B 5/681
2021/0161482 A1* 6/2021 Aizawa ................. G16H 20/70

OTHER PUBLICATIONS

Patel AN, Howard MD, Roach SM, et al. Mental State Assessment and Validation Using Personalized Physiological Biometrics. Front Hum Neurosci. 2018; 12:221 (Year: 2018).*

Ruediger, H., et al., "Sympathetic and parasympathetic activation in heart rate variability in male hypertensive patients under mental stress", Journal of Human Hypertension (2004); 18; pp. 307-315.

Zhong, Yuru, et al., "Quantifying cardiac sympathetic and parasympathetic nervous activities using principal dynamic modes analysis of heart rate variability" Innnovative Methodology, The American Journal of Physiology: Heart and Circulatory Physiology (2006); 291; pp. H1475-H1483.

* cited by examiner

Worker A
- Ok
- Healthy 86%
- Sympathetic/Parasympathetic ratio 95% a.

Worker B
- Recovering
- Healthy 45%
- Sympathetic/Parasympathetic ratio 36% b.

Worker C
- Overloaded
- Health 26%
- Sympathetic/Parasympathetic ratio 32% c.

Worker D
- Ok
- Healthy 83%
- Sympathetic/Parasympathetic ratio 92% d.

Worker E
- Ok
- Health: 89%
- Sympathetic/Parasympathetic ratio 93% e.

Fig. 9

METHOD AND SYSTEM FOR APPORTIONING TASKS TO PERSONS IN ENVIRONMENT

TECHNICAL FIELD

The present subject matter relates to electronic-computing systems and in particular relates to monitoring systems in environment involving human-activity.

BACKGROUND

Institutions and organizations are known to incur significant time, energy, and resources to develop and implement mechanisms for monitoring performance and thereby allocate tasks within the work-force during operations. For example, in a factory, workmen may be evaluated for time-efficiency and skill exhibited during a task-completion. Based on said tests, further work is allocated to achieve an overall-efficiency in the interests of the organization However, such type of analytical-systems usually remain limited to taking into account workmen' timebased efficiencies for task-completion. As a result, the resulting task-allocation remains indifferent to the workman's health and psyche and ends up allocating-work that may prove detrimental to the workman's state. In a worst case scenario, the task-allocation executed irrespective of mental and health state may result in hospitalization or untimely-demise.

In other words, time efficiency shown by the workman towards a task may not indicate as to how the workman had been physiologically and psychologically linked to the task during the performance of task. Moreover, the conventional apportionment based mechanisms refrain from allocating tasks to workman based on a prevailing 'health' (i.e. mental and/or physical state) of a workman.

Accordingly, the conventional task-allocation mechanisms in working-environment usually end up burdening a sick-person with tasks that may take unwanted toll on its health.

Further, the conventional apportioning-mechanisms also fail to predict physiological-behavior of a person in working-environment. In other words, the work-allocation as per the conventional-mechanism completely ends up being based on past recorded events and fails to take into account as to what may be a physiological and psychological state of the workman on any given day.

There lies at-least a need for a mechanism that at-least considers psychological state of a workman as a parameter during apportioning work with respect to a workman.

Further, there lies at-least a need for a mechanism that at-least considers health of a workman as a parameter during apportioning work with respect to a workman.

Furthermore, there lies at least another need for a mechanism that at-least predicts a state of the workman prior to apportioning-work.

Last but not the least, there lies at least a need to provide an improved work-apportioning system in any working environment.

SUMMARY

This summary is provided to introduce a selection of concepts in a simplified format that is further described in the detailed description of the present disclosure. This summary is neither intended to identify key inventive concepts of the disclosure nor is it intended for determining the scope of the invention or disclosure.

In an embodiment, the present subject matter illustrates a method for apportioning tasks to person in an environment. The method comprises capturing a first-value indicating a sympathetic-nerve based activity and a second value indicating a parasympathetic-nerve based activity for at least one person operating in an environment. Thereafter, a quantitative relation is determined between the first and second values. At-least one task is assigned for execution by said person within the environment based on such quantitative relation.

In another embodiment, the present subject matter illustrates another method for apportioning tasks to person in an environment. The present subject matter describes determining a quantitative-relation between the first and second values with respect to at least one person, the first value indicating a sympathetic-nerve based activity and the second value indicating a parasympathetic-nerve based activity for said at least one person operating in an environment. Thereafter, the method comprises computing a complexity associated with respect to at least one task performed within the environment, wherein said complexity is based at least based on a completion-time associated with said at least one task. Further, said at-least one task is assigned for execution by said at-least one person based on said quantitative relation and the computed complexity.

In another embodiment, the present subject matter describes a method for apportioning tasks to person in an environment. The method comprises determining a quantitative-relation between the first and second values with respect to at least one person, the first value indicating a sympathetic-nerve based activity and the second value indicating a parasympathetic-nerve based activity for said at least one person operating in an environment. Further, the method comprises computing a plurality of values with respect to at-least one task performed within the environment, wherein each of said plurality of values denotes a ratio between the sympathetic nerve activity and the parasympathetic nerve activity exhibited by the one or more persons during the performance of said task. Further, the method comprises deriving an overall ratio out of the plurality of computed ratios with respect to said at least one task.

The objects and advantages of the embodiments will be realized and achieved at-least by the elements, features, and combinations particularly pointed out in the claims. It is to be understood that both the foregoing general description and the following detailed description are representative and explanatory and are not restrictive of the invention, as claimed.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 9 illustrates another example illustration depicting task-allocation, in accordance with another embodiment of the present subject matter;

Figure 1:
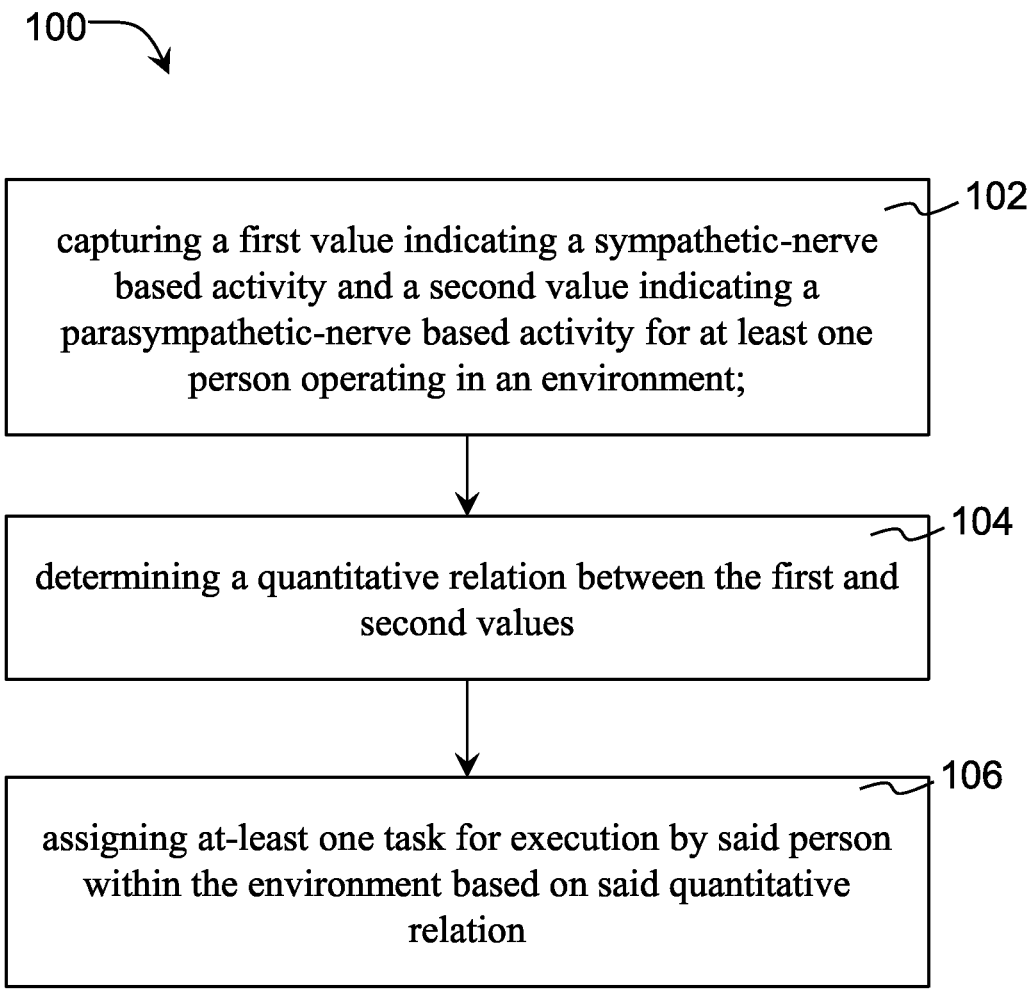
FIG. 1 illustrates a method for apportioning tasks to person in an environment, in accordance with an embodiment of the present subject matter.

The elements in the drawings are illustrated for simplicity and may not have been necessarily been drawn to scale. Furthermore, in terms of the construction of the device, one or more components of the device may have been represented in the drawings by conventional symbols, and the drawings may show only those specific details that are pertinent to understanding the embodiments of the present disclosure so as not to obscure the drawings with details that will be readily apparent to those of ordinary skill in the art having benefit of the description herein.

DETAILED DESCRIPTION OF SOME EXAMPLE EMBODIMENTS

For the purpose of promoting an understanding of the principles of the present disclosure, reference will now be made to the embodiment illustrated in the drawings and specific language will be used to describe the same. It will be understood that no limitation of the scope of the present disclosure is thereby intended, such alterations and further modifications in the illustrated system, and such further applications of the principles of the present disclosure as illustrated therein being contemplated as would normally occur to one skilled in the art to which the present disclosure relates.

The foregoing general description and the following detailed description are explanatory of the present disclosure and are not intended to be restrictive thereof.

Reference throughout this specification to "an aspect", "another aspect" or similar language means that a particular feature, structure, or characteristic described in connection with the embodiment is included in at least one embodiment of the present disclosure. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or subsystems or elements or structures or components proceeded by "comprises . . . a" does not, without more constraints, preclude the existence of other devices or other subsystems or other elements or other structures or other components or additional devices or additional subsystems or additional elements or additional structures or additional components.

Unless otherwise defined, all technical and scientific terms used herein have the same meaning as commonly understood by one of ordinary skill in the art to which this present disclosure belongs. The system, methods, and examples provided herein are illustrative only and not intended to be limiting.

FIG. 1 illustrates a method for apportioning tasks to person in an environment. In an example, said person may be a workman or a professional and the environment may be a working-environment. The method comprises capturing (step 102) a first-value indicating a sympathetic-nerve based activity and a second-value indicating a parasympathetic-nerve based activity for at-least one person operating in an environment. The first and second-values are activity-levels with respect to the respective-nerve, said activity levels having been calculated from historical biometric-information of the person.

The historical biometric-information of the person is defined in terms of one or more of heart-rate, respiration-rate, blood-pressure, body-temperature, skin conductance, and Electroencephalography (EEG) data. Further, such historical biometric-information is captured through at-least one sensor-device defined by one or more of heart rate sensors, a respiration sensor, a blood-pressure measuring device, EEG apparatus, a wristband, an optical head-mounted display unit, wearables having embedded sensors, a smart phone capable of capturing physiological parameters.

As a part of gathering the biometric information, an activity-level of the sympathetic nerve of the person and the activity level of the parasympathetic-nerve are calculated (step 104) according to heart-rate information of the person. The activity-level of the sympathetic nerve of the person is calculated according to a first frequency component (e.g. a higher-frequency) included in heart-rate information and the activity level of the parasympathetic nerve of the person is calculated according to a second frequency component lower than the first frequency included in the heart rate information.

In an example and without limiting the scope of the present subject matter, the activity-levels of sympathetic-nerve and parasympathetic-nerve are determined based on heart rate variability (HRV) measurements. Heart Rate Variability (HRV) is known to reflect the balance between the Sympathetic and Parasympathetic nervous system. When in Parasympathetic mode, workers cannot handle difficult tasks (slower to complete and higher chance of mistakes). When in Sympathetic mode, workers are better at handling challenging tasks. SP ratio fluctuates during the day and it is unique for each person.

HRV may be measured using electrocardiography (ECG or EKG). The electrocardiogram represents the cardiac-cycle as a wave with four major parts: a P wave, a QRS complex, a T wave, and a U wave. The HRV may be measured as the variation in duration between the R peaks on the QRS complexes over consecutive cardiac cycles. The variability of the RR interval may be measured in various ways, usually using time-domain methods, which determine the intervals of cardiac cycles. Under frequency domain methods, HRV may be studied in the frequency-domain by converting heart rate (time domain) to a power spectrum (frequency domain) using a mathematical algorithm called the Fourier transformation.

Further, in another example, the HRV is analyzed using HRV associated with decreasing (decelerating) heart rate. In another example, yet another method of determining HRV includes Photoplethysmography (PPG), wherein the plethysmogram waveform represents pulsatile peripheral blood flow. The same reflects both peripheral and central hemodynamics. PPG employs infrared light (IR) transmitted through the skin to noninvasively measure hemodynamic parameters, thereby being a useful measure of vascular dysfunction and heart rate variability.

Further, a quantitative relation is determined (step 104) between the first and second values. The quantitative relation represents at-least one or more of a ratio, percentage, fraction, rate, proportion, relative magnitude, scale. The determination of the quantitative-relation comprises predicting the quantitative-elation from the first and second value through a first machine leaning criteria. Such quantitative-relation may be predicted as a time-varying pattern for a given working day.

Based on the predicted quantitative-relation between the first and second values, at-least one task is assigned (step 106) for execution by said person within the environment based on said quantitative-relation. Such an assignment of task to said at-least one person is based on a mapping between a complexity associated with said task to be assigned, and the determined quantitative relationship. In an example, such complexity associated with the task may be defined by at least one of: time-duration required for task-completion, probability of failure, level of skill set required, a magnitude of resources required, expected energy consumption, and infrastructure requirement.

In an example, to apply such mapping, an optimization-criteria may be executed to strike a balance between the quantization ratio and the complexity of the task during the task-allocation. Such assignment of said at-least one task to said at least one person further comprises displaying a pre-determined day's time-table for said at least one person for completing a plurality of tasks within a predetermined time period for a day, said time-table identifying time-slots allocated to the assigned tasks. In an example, a time-table for a particular-worker may be prepared for any given day (say a "forthcoming day") for listing the allocated time-slots in any given day for a particular task. An example illustration has been depicted in FIG. 7 and FIG. 8.

Figure 2:
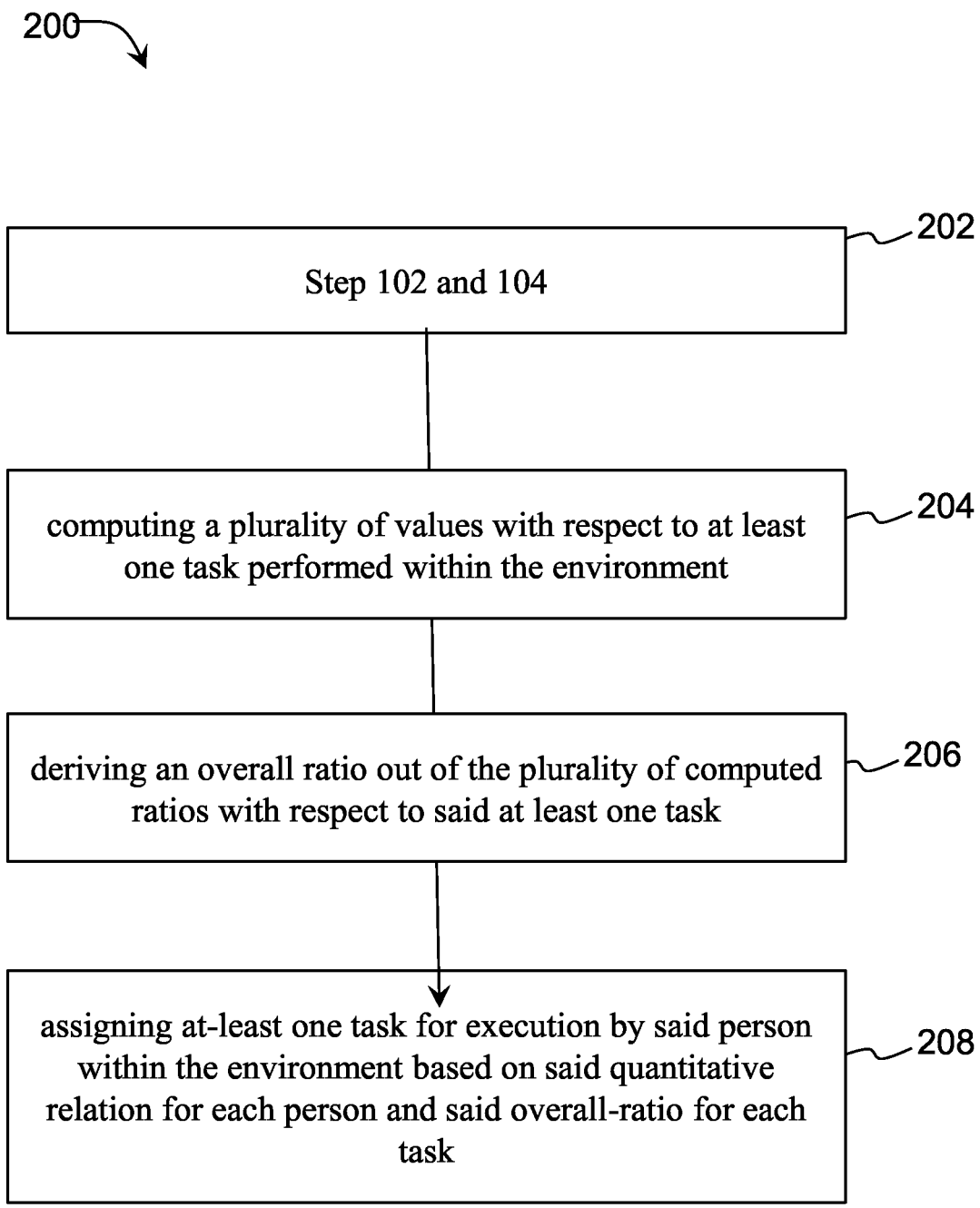
FIG. 2 illustrates a method for apportioning-tasks to person in an environment, in accordance with an embodiment of the present subject matter.

FIG. 2 illustrates a method for apportioning-tasks to person in an environment, in accordance with another or second embodiment of the present subject matter. The method comprises capturing (step 202) a first-value indicating a sympathetic-nerve based activity and a second-value indicating a parasympathetic-nerve based activity for at-least one person operating in an environment and determining a quantitative relation between the first and second values, thereby being analagous to the steps 102 and 104 of FIG. 1.

Further, the method comprises step computing a plurality of values (204) with respect to said at-least one task, wherein each of said plurality of values denotes a ratio between the sympathetic nerve activity and the parasympathetic nerve activity exhibited by the one or more persons during the performance of said task. Said plurality of values for each task may correspond to heart rate variability (HRV) information as exhibited by different workmen or professionals during the performance of said task. More specifically, the plurality of values for each task may be obtained from the same data (i.e. historical biometric information observed in the working environment) as has been used to measure or predict the SP-profiles for different persons in FIG. 1.

Thereafter, the method comprises computing (step 208) a minimum-ratio out of the plurality of computed ratios with respect to said at least one task. Such computation of the minimum-ratio comprises predicting the ratio out of the plurality of ratios for said at least one task through a second machine leaning criteria. In other words, the present step computes an SP profile as required to be exhibited by a professional for each task.

Further, the method comprises assigning (step 210) said at-least one task based on said predicted SP-ratio and the predicted SP profile. In order to execute said assignment of tasks based on said two factors, any known optimization-criteria may be applied over said two factors: a) predicted SP ratio and b) the minimum ratio to achieve an optimized balance between the duo while allocating-tasks.

Figure 3:
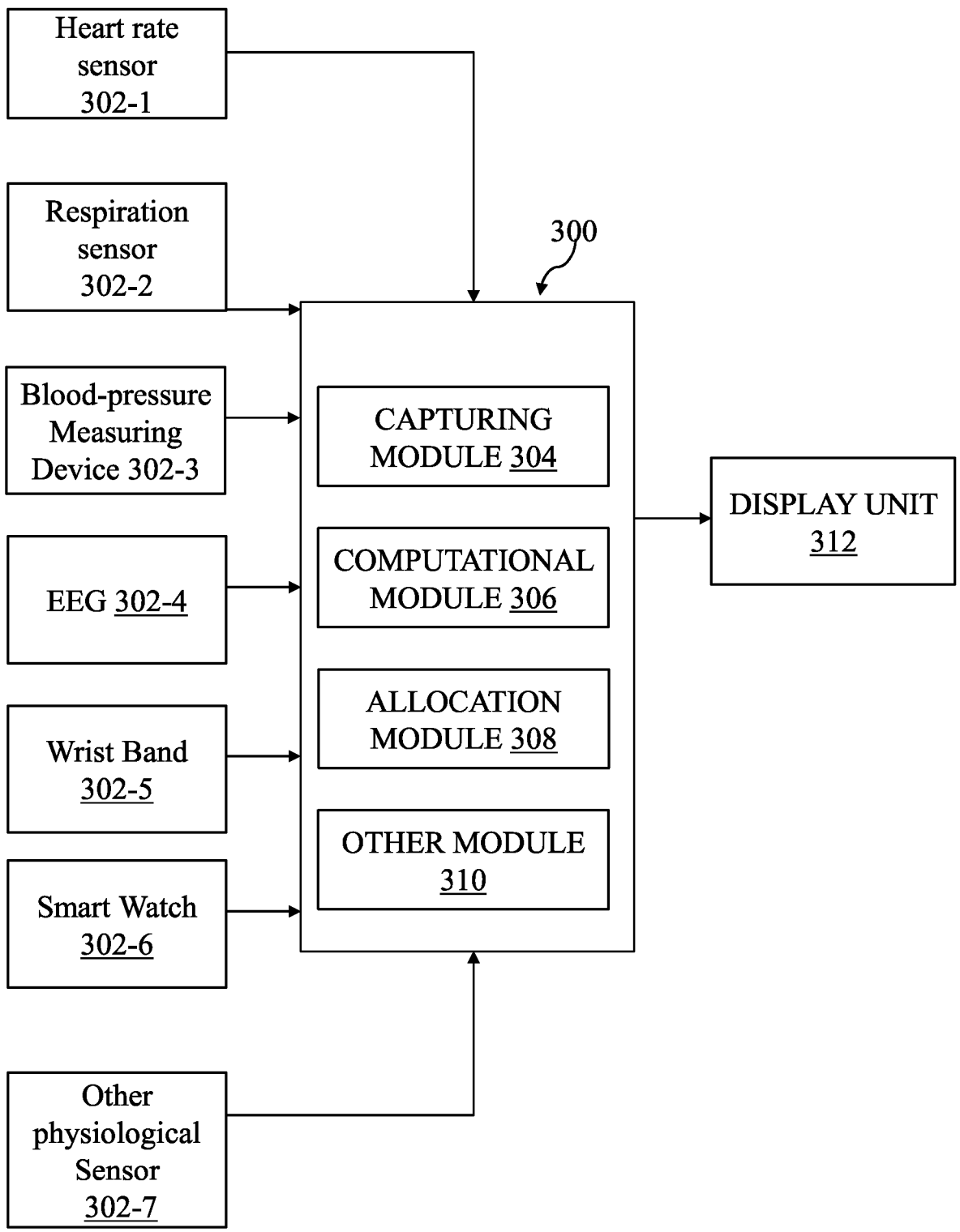
FIG. 3 illustrates a schematic-architecture for apportioning-tasks in a working environment, in accordance with an embodiment of the present subject matter.

FIG. 3 illustrates a schematic-architecture for apportioning-tasks in a working environment. The architecture comprises a set of physiological sensors 302-1 to 7 for measuring physiological parameters with respect to the workmen. In an example, said sensors may be heart rate sensor, blood pressure measuring sensor, respiration sensor, EEG, wristband, smartwatch etc. The input from the sensors 302 are received by an apportioning system 300 that comprises a data-capturing module 304 executing the method step 102. A computing-module 304 executes the computational-steps 104, 204 and 206. A task-allocation module 306 executes the steps 106, 208. The miscellaneous or other module 208 facilitates cooperation among the modules 302, 304, 306 and 308. Further, a display module provides the representation as has been depicted in an example by FIG. 7 and FIG. 8. Overall, in an embodiment, the apportioning system 300 is configured to execute the method steps 102 till 106 as depicted in FIG. 1. In another embodiment, the apportioning system 300 is configured to execute the method steps 202 till 208 as depicted in FIG. 2.

Figure 4A:
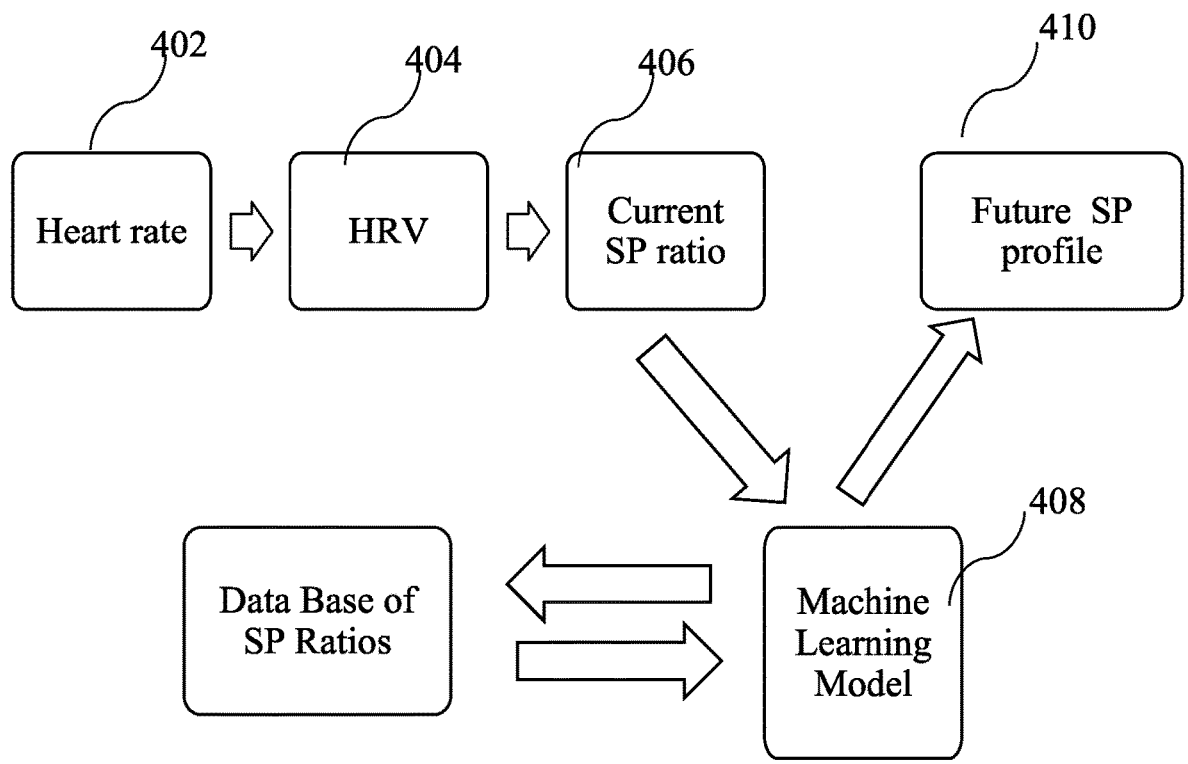
FIG. 4A and FIG. 4B illustrate example-implementation of the method steps of FIG. 1, in accordance with an embodiment of the present subject matter.

FIG. 4A illustrates an example implementation of the method steps of FIG. 1, in accordance with an embodiment of the present embodiment. More specifically, the steps of FIG. 4A correspond to steps 102 and 104 of FIG. 1.

At step 402, the heart-rate is captured as example physiological-parameter.

At step 404, the heart-rate variability is computed from the captured physiological-parameters as has been depicted as a part of preceding description.

At step 406, the current SP ratio is calculated from the currently-measured physiological-parameters i.e. Heart-rate information and Hear rate variability (HRV) with respect to a particular-person.

At step 408, a machine learning criteria or any other fuzzy logic based criteria is executed to predict a future SP profile for any given day. In other example, such prediction may be done during early hours of any given day with respect to remaining part of said given day. In other example, the prediction may also be done for forthcoming day such as tomorrow, day after tomorrow, or any other forthcoming-day in future.

In order to predict said future value, the machine-leaning criteria may draw inferences based on a comparison of the current SP ratio with respect to a most-relevant SP ratio obtained in the historical-past. Said most relevant value may be selected from a database of known SP ratios or historical SP-ratios with respect to the currently-measured SP ratio. For example, criteria labelled as Dynamic Time Wrapping Nearest Neighbour (DTW-NN) search may be used to extract the most relevant SP-ratio from the database of historical-SP ratios. In other example, neural-network may be applied for such derivation of known SP ratio from the database.

At step 410, the predicted future SP-profile of the at least one person may be obtained. Said predicted SP profile is associated with any given day. For example, the predicted SP profile may be for today, a portion of today, tomorrow, day after tomorrow, etc.

Likewise, steps 402 till 410 keep on recurring for other persons throughout the day or during a major portion of any working day to cover all of the persons or professionals targeted to be evaluated.

Figure 4B:
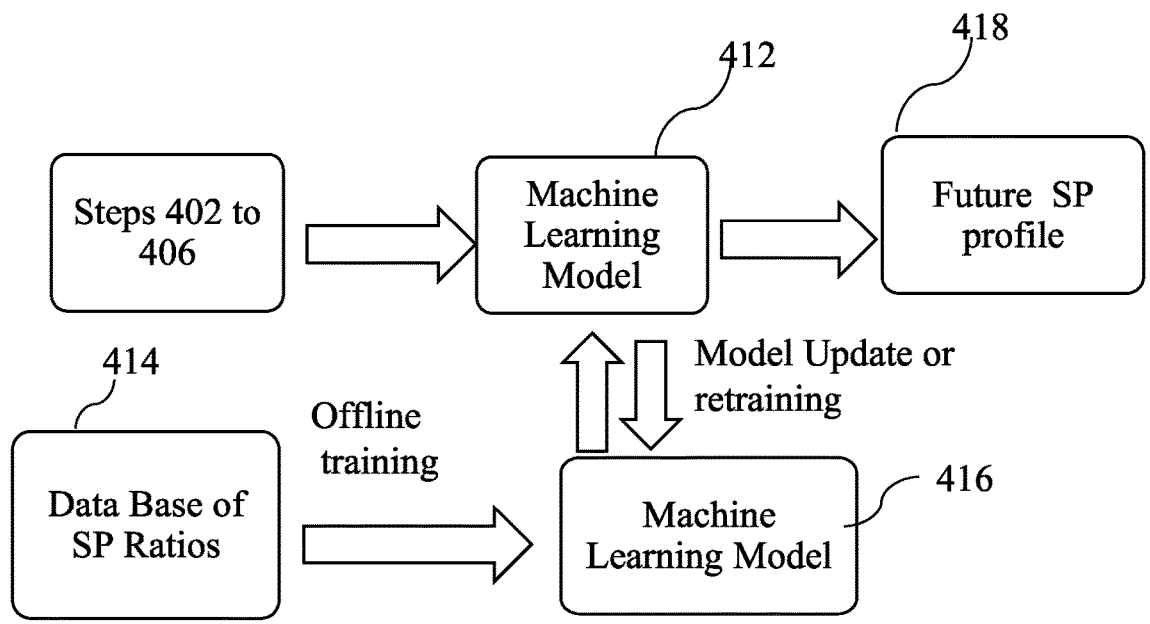

FIG. 4B illustrates another example implementation of the method steps of FIG. 1, in accordance with an embodiment of the present embodiment. More specifically, the steps of FIG. 4 correspond to steps 102 and 104 of FIG. 1.

Step 402 to steps 406 are equivalent to the steps recited in FIG. 4A.

At step 412, the current SP ratio is captured and recorded in real time and processed by the machine learning model in order to predict a future SP profile of the person. However, unlike FIG. 4A where the machine-learning model draws a comparison with the most relevant SP value from the database, FIG. 4B illustrates predicting the profile based on different machine-learning (ML) model criteria, wherein the model is progressively adapted to be in-line with the newly generated SP ratios.

In an example, autoregressive integrated moving average (ARIMA) based models can be used to predict the SP-profile. More specifically, the 'machine learning model' in step 412 predicts the future-SP profile based on training imparted as part of factory settings or in an offline state (i.e. non real-time operation). Said imparting of training or model-update has been depicted with respect to steps 414 and 416.

At step 418, a future SP value is predicted for a person based on the ML model. As may be understood, the future SP value pertains to forthcoming time period, which in an example may be an approaching time period of the present day, tomorrow or day after tomorrow. In case said predicted value substantially diverges with respect to the currently measured actual SP values of the person and accordingly defines a 'TRUTH' condition otherwise associated with the existing model in light of the current captured SP values. Thereafter, optionally a trigger is sent for enabling occurrence of the OFFLINE steps 414 and 416 in order to re-train the existing machine-learning model to generate TRUE values.

At step 414, the database of SP ratios is continuously-updated with the captured SP values including the latest predicted SP value.

At step 416, the machine learning model of step 412 (as based on ARIMA in an example) may be updated to be in line with the newly acquired SP ratios within the database. More specifically, the ML model is updated OFFLINE to fit or be in-line with the changed SP ratios and avoid FALSE generations.

Figure 5:
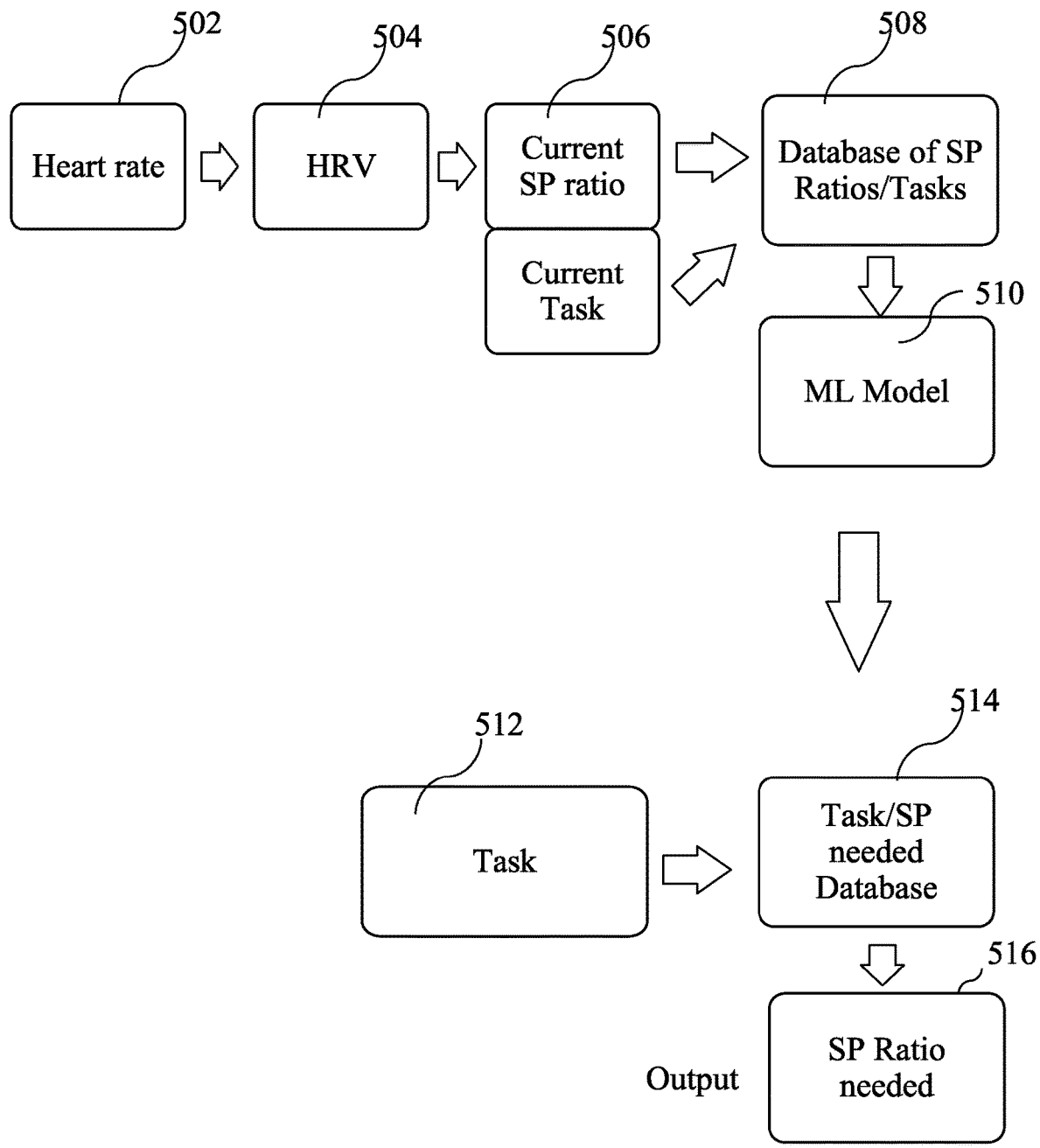
FIG. 5 illustrates an example implementation of the method steps of FIG. 2, in accordance with an embodiment of the present subject matter.

FIG. 5 illustrates an example implementation of the method steps of FIG. 2, in accordance with an embodiment of the present embodiment. More specifically, the steps 502 till 510 represent training of a neural network to predict SP ratio for a task and accordingly depicts an OFFLINE process. However, steps 512 till 516 depict a real-time or online process for predicting SP-ratios for task. Further, the steps of FIG. 5 correspond to steps 202 till 206 of FIG. 2.

Steps 502, 504 correspond to steps 404 and 406. However, the heart-rate and HRV in steps 502 and 504 is now captured in respect of single task with respect to a plurality of persons.

Step 506 corresponds to capturing the SP ratio exhibited during the particular-task performance. For such purpose, the SP ratio as captured during and before and during task is duly noted. Optionally, the task may be evaluated on continuous-metric as a success/failure. Accordingly, the SP ratio for successfully completed tasks is duly recorded and ignored for non-successful task. Alternatively, wherein the success or failure may not be determined, any increase or decrease of SP ratio beyond a threshold value may be ignored for consideration.

Step 508 depicts storage of the valid SP-values as per step 506 within the database as exhibited during the performance of the task in a database.

Step 510 comprises statistically capturing a variation of the SP-values with respect to a certain-task. In an example, using a sliding-window, statistical features (minimum, maximum, average, standard deviation) may be computed by machine-learning (ML) criteria for capturing the fluctuation of the SP-ratio during task-completion. Based thereupon, a neural-network may be trained and stored as a relational-database to predict SP-values required for any given task In another example, an overall complexity associated with the task is predicted based on the captured SP values. Other parameters for complexity prediction may be time-duration required for task-completion, probability of failure, level of skill set required, a magnitude of resources required, expected energy consumption, and infrastructure requirement. In yet other example, the trained neural-network stored within the database may be used to monitor performance of task over a time-period during the task-performance.

The following steps now depict a real-time operation performed in real-time or ONLINE.

Step 512 represents a real-time operation wherein a given-task is provided.

Step 514 represents executing the trained neural network (stored as a database) to predict the SP ratio variation for the given task in hand.

Step 516 represents achieving the predicted SP-ratio for the pre-determined task or an overall complexity associated with the task. In other example, instead of achieving the predicted SP ratio, a person's performance with respect to the task may be measured over a period of time.

Further, in another embodiment, for extreme cases where the task is non-repetitive and is merely performed once in a while, the captured SP-values for the task-data is not available. In other scenario, owing to sudden-changes in work-plan, the tasks itself may undergo change. In such a scenario, a manual procedure may be adopted wherein the SP-ratio may be instead manually-generated. For instance, a supervisor or a line-manager may assess the task's difficulty or complexity manually. Based thereupon, the required SP-ratio needed for the task is calculated. Accordingly, an appropriate time for execution of the task may be further calculated and a right-professional may be mapped with respect to the task. Difficult-tasks (i.e. tasks which have been manually-rated) are then automatically scheduled for execution by employees during sympathetic mode, while substantially less complex tasks may be scheduled for execution during parasympathetic mode.

Figure 6:
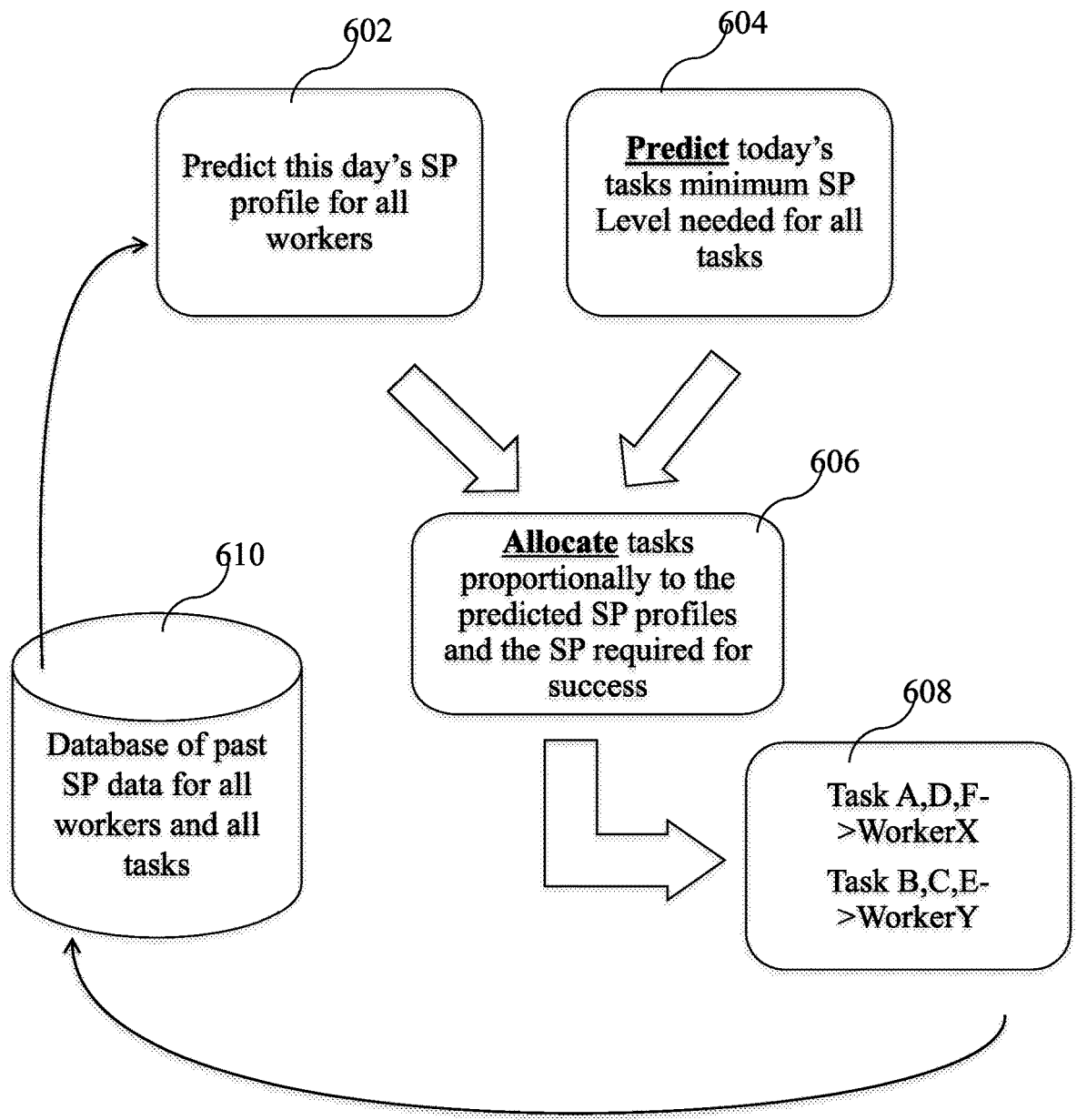
FIG. 6 illustrates a further example implementation of the method steps of FIG. 1 and FIG. 2, in accordance with an embodiment of present subject matter.

FIG. 6 illustrates a further example implementation of the method steps of FIG. 1 and FIG. 2, in accordance with an embodiment of the present embodiment. More specifically, the steps 602 till 610 represent the allocation of the tasks to the professionals based on the predicted SP values for the professional and the task. The present steps 602 to 610 correspond to steps 102 to 106 of FIG. 1 and steps 202 till 208 of FIG. 2.

Steps 602 and 604 represent the example-embodiment as depicted FIG. 4A, FIG. 4B and FIG. 5, and accordingly depict the predicted SP ratio for the individual and the tasks.

Step 606 represents allocation of the tasks proportionally to the professionals based on the predicted SP-profiles for each of the professional and the each of the task. More specifically, the tasks are allotted based on an optimization algorithm as applicable to the both types of computed SP ratios.

As may be understood, the 'allocation of tasks among the workers or professionals' may be defined as a problem, which is subject to various constraints. In an example, an objective function may be a cost-function which is to be minimized to address the problem of task-allocation. Said cost-function may be defined as difference between the SP needed to complete a task and the predicted SP with respect to the worker for the given time-slot. The cost-function may be 0 if the predicted SP ratio is greater than the min SR. In the present matter, a minimum-value of SP needed for each task constitutes the set of soft constraints. Accordingly, the minimization of cost function in an example may be executed using Linear Programming techniques, thereby overcoming the problem of task allocation among the workers.

Step 608 represents the task-allocation to each professional in the organization. Said task-allocation has been depicted in an example through the diagrammatic-representation as provided in FIG. 7 and FIG. 8. In an example, task-allocation may be optimized, wherein more important tasks are allocated to professionals in fine-health and in respect of whom the predicted SP ratio is high at a given time-slot. Lesser important tasks which require low SP may be allocated to professionals whose SP ratio is low and are accordingly stressed-out.

Step 610 represents the database storing the historical and predicted SP-values for the professionals and the tasks for the purposes of execution of the steps 602 and 604.

Figure 7:
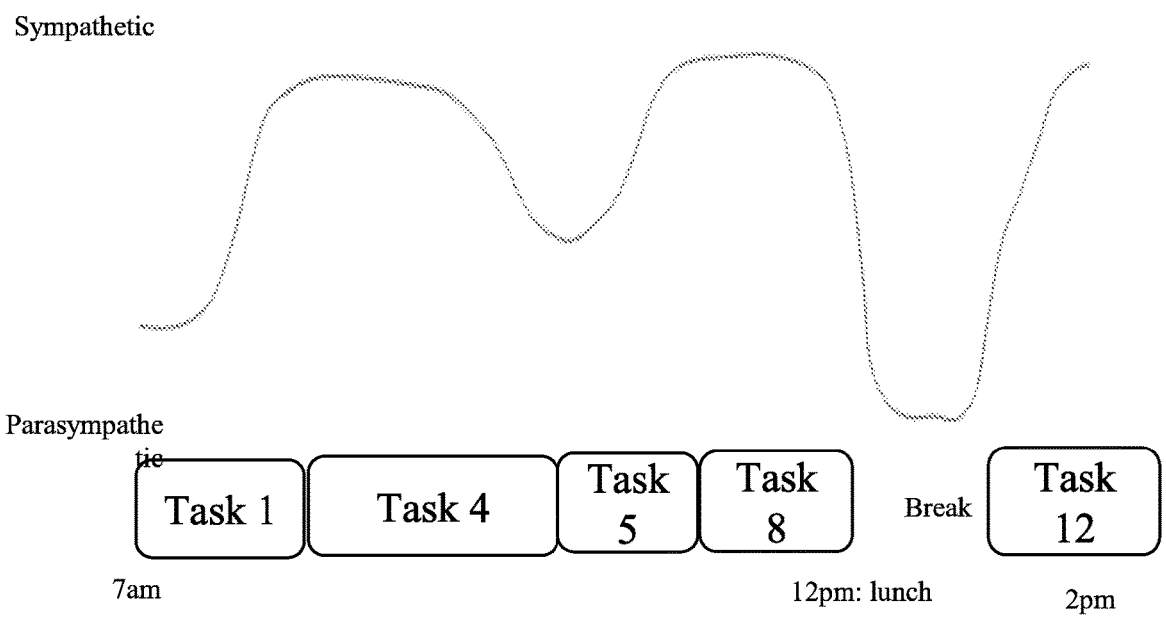
FIG. 7 illustrates an example representation depicting task-allocation, in accordance with another embodiment of the present subject matter.

FIG. 7 represents an example representation depicting task-allocation to the person A based on the predicted SP profile.

For example, in FIG. 7, the tasks (Task 1, 4, 5, 8 and 12) are allocated based on the predicted SP profile of a person A having various time-slots wherein SP rises high and other time-slots wherein the SP lowers down. There are some tasks 4, 8 and 12 in respect of which the difficulty or complexity level is HIGH. Alternatively, for the tasks 4, 8 and 12, the predicted SP value has been found to be HIGH. Accordingly, the tasks 4, 8 and 12 are allocated to the person A with respect to high SP value. In other words, the time-zones of the day where high SP-ratio from the person is expected are reserved for performance of high SP rated tasks.

Further, the tasks (Tasks 1 and 5) are allocated based on the predicted SP-profile of a person A, said task-allocation occurring during various time-slots wherein SP lowers down. More clearly, for the tasks 1 and 5, the predicted SP value has been found to be LOW. Accordingly, said tasks 1 and 5 are allocated to the person A with respect to low SP values. In other words, the time-zones of the day where low SP-ratio from the person is expected are reserved for performance of low SP rated tasks.

Figure 8:
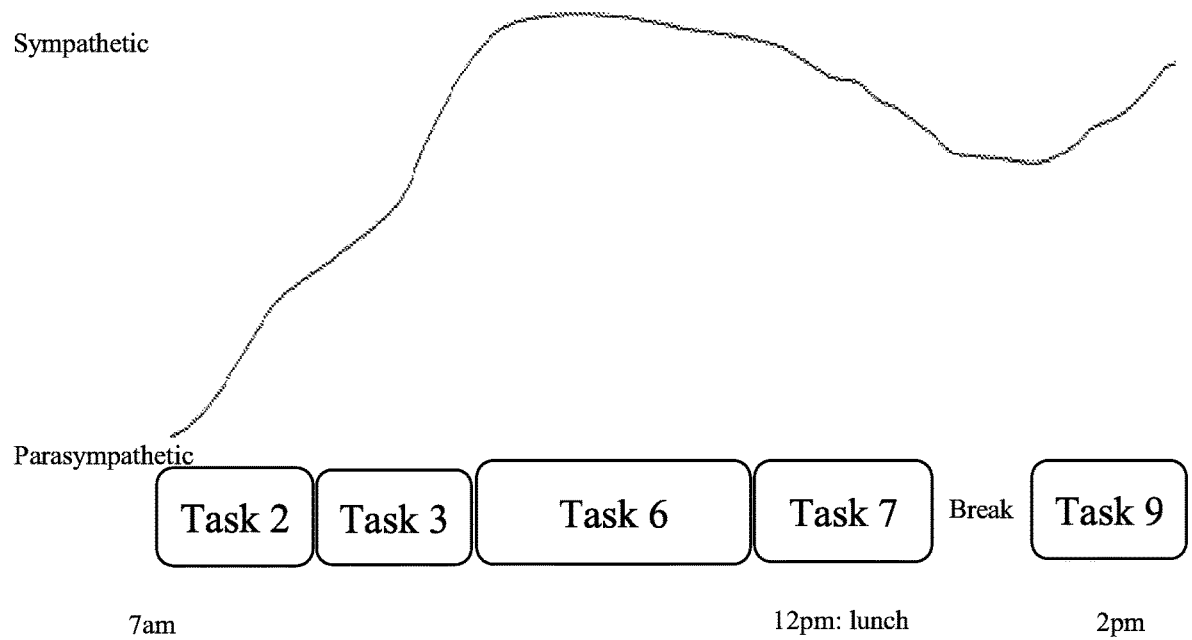
FIG. 8 illustrates another example representation depicting task-allocation, in accordance with another embodiment of the present subject matter.

FIG. 8 represents an example representation depicting task-allocation to the person B based on the predicted SP profile. In FIG. 8, the tasks (Task 2, 3, 6, 7 and 9) are allocated based on the predicted SP profile of a person 'B' having various time-zones wherein SP rises high and other time zones wherein the SP lowers down. There is a task 6 in respect of which the difficulty or complexity-level is high. In other example, for the task 6, the predicted SP value has been found to be HIGH. Accordingly, the task 6 is allocated to the person B with respect to high SP values. In other words, the time-slots of the day, where high SP-ratio from the person have been predicted, are reserved for performance of high SP rated tasks.

Further, the tasks (Tasks 2, 3, 7 and 9) are allocated based on the predicted SP-profile of a person 'B' having various time-zones wherein SP lowers down. More clearly, for the tasks 3, 7 and 9, the predicted SP value has been found to be LOW. Accordingly, said tasks 3, 7 and 9 are allocated to the person B with respect to low SP values. In other words, the time-zones of the day where low SP-ratio from the person B is expected are reserved for performance of low SP rated tasks. Furthermore, the task 1 having the minimum associated SP ratio is allocated to such time-zones of day where the person B exhibits minimum SP ratio (i.e. the person is actually stressed out).

FIG. 9 illustrates an example illustration depicting the predicted SP ratios for every professional or worker (say worker 1 to worker 8) along with the health conditions as have been also determined from the physiological parameters Accordingly, based on the predicted SP ratio and optionally based on the determined health conditions of the person, or a combination thereof, the different tasks are allocated to different professionals.

In an example, Worker A having 91% SP and being 86% healthy is considered FIT and may be awarded a high SP ranked task. Worker B having 45% SP and being 36% healthy is considered as "recuperating" and may be awarded a low SP ranked task. Worker C having 32% SP and being 26% healthy may be considered as "stressed out" and awarded a substantially low SP ranked task. Worker D having 92% SP and being 83% healthy may be considered as "FIT" and awarded a high SP ranked task. Likewise, Worker E having 93% SP and being 89% healthy may be considered as "Extremely FIT" and awarded a substantially high SP ranked task.

As may be understood, when in Parasympathetic mode, people cannot handle difficult-tasks. If awarded difficult tasks during Parasympathetic mode, people are not only slower to complete, but also exhibit higher-chance of mistakes. In Sympathetic-mode, the professionals are better at handling challenging-tasks and accordingly take shorter to complete any given task.

The representation in FIG. 9 at-least takes into account aforesaid guidelines while allocating tasks based on aforesaid predicted SP profiles of the person, task, and other parameters such complexity of the task. The SP profile as predicted by the present subject matter with respect to a professional day captures the fluctuation of SP ratio for a given time period, wherein the SP profile differs from one person to another. Overall, the predicted SP ratio is used as indicia to predict how well a person will perform certain-tasks at a certain time. Further, the predicted SP ratio also is further used an indicia to predict how complex a task might be and which person or time-zone of the day (or both) may be utilized to achieve a satisfactory performance of the task.

At-least as a result of the present subject matter, a pre-determined day's time-table is displayed for said at-least one person for completing a plurality of tasks within a predetermined time period for a day. The time-table identifies time-slots allocated to the assigned tasks. This at least enables optimization worker-shifts within an organization to maximize productivity, wherein such optimization is done at least based on skillsets of the worker and heart-rate information as noted with respect to the worker during performance of tasks.

Overall, the task-allocation as executed by the present subject matter is customized to each worker's physiological characteristics, thereby facilitating increment in productivity, minimization of mistakes, better quality of work etc.

Figure 10:
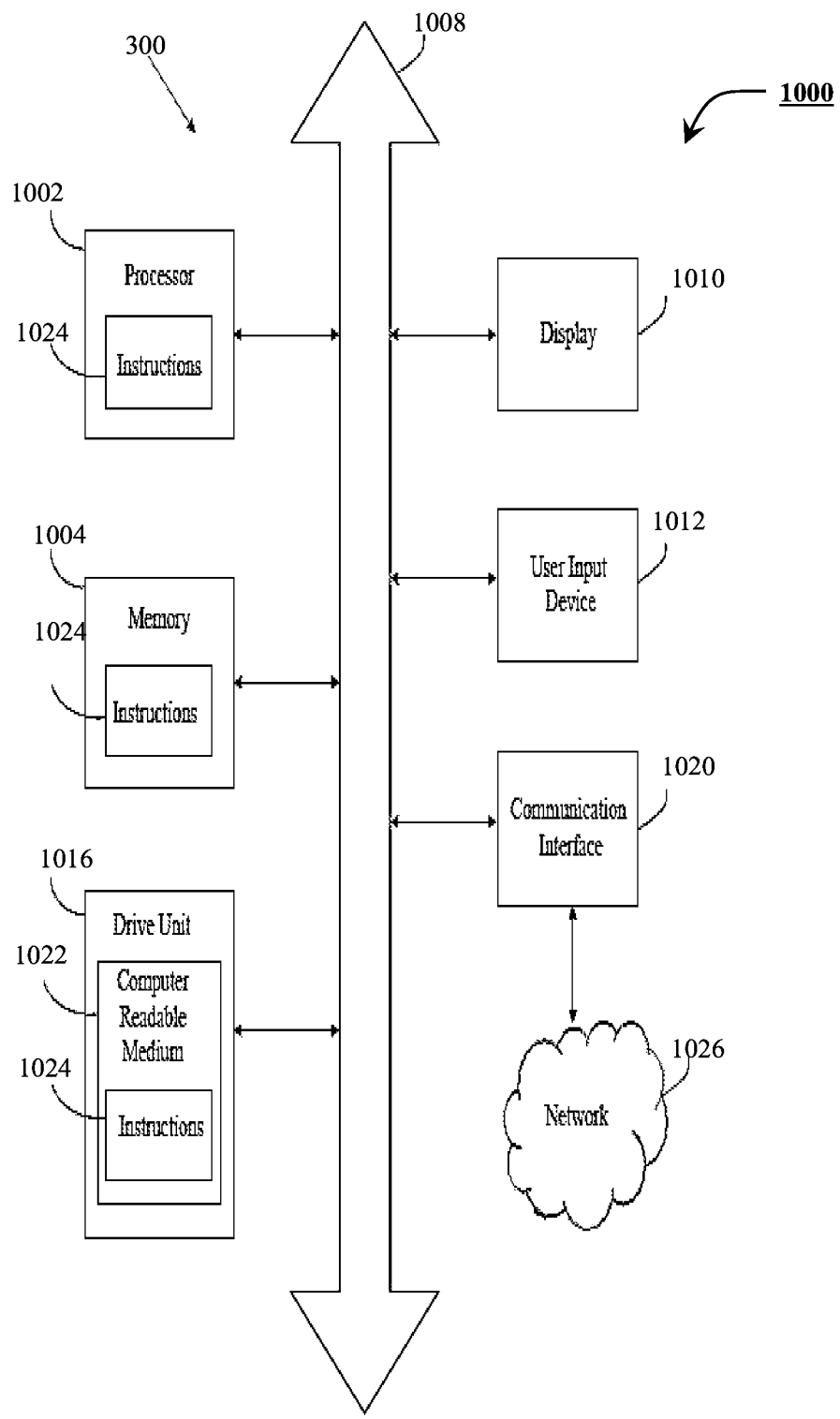
FIG. 10 illustrates an implementation of the apportioning system in a computing environment, in accordance with another embodiment of the present subject matter.

FIG. 10 illustrates an implementation of the apportioning system 300 as illustrated in FIG. 3 in a computing environment. The present figure essentially illustrates the hardware configuration of the system 300 in the form of a computer system 1000 is shown. The computer system 1000 can include a set of instructions that can be executed to cause the computer system 1000 to perform any one or more of the methods disclosed. The computer system 1000 may operate as a standalone device or may be connected, e.g., using a network, to other computer systems or peripheral devices.

In a networked deployment, the computer system 1000 may operate in the capacity of a server or as a client user computer in a server-client user network environment, or as a peer computer system in a peer-to-peer (or distributed) network environment. The computer system 1000 can also be implemented as or incorporated into various devices, such as a personal computer (PC), a tablet PC, a personal digital assistant (PDA), a mobile device, a palmtop computer, a laptop computer, a desktop computer, a communications device, a wireless telephone, a land-line telephone, a web appliance, a network router, switch or bridge, or any other machine capable of executing a set of instructions (sequential or otherwise) that specify actions to be taken by that machine. Further, while a single computer system 1000 is illustrated, the term "system" shall also be taken to include any collection of systems or sub-systems that individually or jointly execute a set, or multiple sets, of instructions to perform one or more computer functions.

The computer system 1000 may include a processor 1002 (e.g., a central processing unit (CPU), a graphics processing unit (GPU), or both. The processor 1002 may be a component in a variety of systems. For example, the processor 1002 may be part of a standard personal computer or a workstation. The processor 1002 may be one or more general processors, digital signal processors, application specific integrated circuits, field programmable gate arrays, servers, networks, digital circuits, analog circuits, combinations thereof, or other now known or later developed devices for analyzing and processing data The processor 1002 may implement a software program, such as code generated manually (i.e., programmed).

The computer system 1000 may include a memory 1004, such as a memory 1004 that can communicate via a bus 1008. The memory 1004 may be a main memory, a static memory, or a dynamic memory. The memory 1004 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one example, the memory 1004 includes a cache or random access memory for the processor 1002. In alternative examples, the memory 1004 is separate from the processor 1002, such as a cache memory of a processor, the system memory, or other memory. The memory 1004 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 1004 is operable to store instructions executable by the processor 1002. The functions, acts or tasks illustrated in the figures or described may be performed by the programmed processor 1002 executing the instructions stored in the memory 1004. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown, the computer system 1000 may or may not further include a display unit 1010, such as a liquid crystal display (LCD), an organic light emitting diode (OLED), a flat panel display, a solid state display, a cathode ray tube (CRT), a projector, a printer or other now known or later developed display device for outputting determined information. The display 1010 may act as an interface for the user to see the functioning of the processor 1002, or specifically as an interface with the software stored in the memory 1004 or in the drive unit 1016.

Additionally, the computer system 1000 may include an input device 1012 configured to allow a user to interact with any of the components of system 1000. The input device 1012 may be a number pad, a keyboard, or a cursor control device, such as a mouse, or a joystick, touch screen display, remote control or any other device operative to interact with the computer system 1000.

The computer system 1000 may also include a disk or optical drive unit 1016. The disk drive unit 1016 may include a computer-readable medium (CRM) 1022 in which one or more sets of instructions 1024, e.g. software, can be embedded. The instructions 1024 stored within the CRM 1022 upon execution cause the computer system 1000 to execute the method steps 102 to 106. In other example, the instructions 1024 stored within the CRM 1022 upon execution cause the computer system 1000 to execute the method steps 202 to 208. Further, the instructions 1024 may embody one or more of the methods or logic as described. In a particular example, the instructions 1024 may reside completely, or at least partially, within the memory 1004 or within the processor 1002 during execution by the computer system 1000. The memory 1004 and the processor 1002 also may include computer-readable media as discussed above.

The present invention contemplates a computer-readable medium that includes instructions 1024 or receives and executes instructions 1024 responsive to a propagated signal so that a device connected to a network 1026 can communicate voice, video, audio, images or any other data over the network 1026. Further, the instructions 1024 may be transmitted or received over the network 1026 via a communication port or interface 1020 or using a bus 1008. The communication port or interface 1020 may be a part of the processor 1002 or may be a separate component. The communication port 1020 may be created in software or may be a physical connection in hardware. The communication port 1020 may be configured to connect with a network 1026, external media, the display 1010, or any other components in system 1000 or combinations thereof. The connection with the network 1026 may be a physical connection, such as a wired Ethernet connection or may be established wirelessly as discussed later. Likewise, the additional connections with other components of the system 1000 may be physical connections or may be established wirelessly. The network 1026 may alternatively be directly connected to the bus 1008.

The network 1026 may include wired networks, wireless networks, Ethernet AVB networks, or combinations thereof. The wireless network may be a cellular telephone network, an 802.11, 802.16, 802.20, 802.1Q or WiMax network. Further, the network 1026 may be a public network, such as the Internet, a private network, such as an intranet, or combinations thereof, and may utilize a variety of networking protocols now available or later developed including, but not limited to TCP/IP based networking protocols.

In an alternative example, dedicated hardware implementations, such as application specific integrated circuits, programmable logic arrays and other hardware devices, can be constructed to implement various parts of the system 1000.

Terms used in this disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description of embodiments, claims, or drawings, should be understood to contemplate the possibilities of including one of the terms, either of the terms or both terms. For example, the phrase "A or B" should be understood to include the possibilities of "A" or "B" or "A and B."

All examples and conditional language recited in this disclosure are intended for pedagogical objects to aid the reader in understanding the invention and the concepts contributed by the inventor to furthering the art and are to be construed as being without limitation to such specifically recited examples and conditions. Although embodiments of the present disclosure have been described in detail, it should be understood that various changes, substitutions, and alterations could be made thereto without departing from the spirit and scope of the present disclosure.

The invention claimed is:

1. A method for apportioning tasks to a person in an environment, the method comprising:
receiving heart rate information of the person obtained by a heart rate monitor;
calculating, by using a computer, a sympathetic activity level of a sympathetic nerve of the person according to a first frequency component included in the heart rate information and a parasympathetic activity level of a parasympathetic nerve of the person according to a second frequency component lower than the first frequency included in the heart rate information;
calculating, by using the computer, a ratio between the sympathetic activity level and the parasympathetic activity level;
predicting, by a machine learning process by using the computer, a change in the ratio within a predetermined time period for the person, wherein in the machine learning process, a machine leaning criteria draws inferences based on a comparison of the ratio with respect to a most-relevant ratio obtained in historical data; and
allocating, by using the computer, one or more tasks for execution by the person within the predetermined time period based on the calculated ratio and the predicted change in the ratio,
wherein the method further comprises:
computing, by using the computer, a plurality of ratios between the sympathetic activity level and the parasympathetic activity level with respect to tasks exhibited by one or more persons during performance of the at least one task;
computing, by using the computer, a minimum ratio out of the plurality of computed ratios and a corresponding one of the tasks; and
assigning, by using the computer, the one of the tasks corresponding to the minimum ratio for execution by the person within the predetermined time period, and
the machine learning process comprises:
acquiring a current ratio between the sympathetic activity level and the parasympathetic activity level using a wearable electronic device, wherein the wearable electronic device includes a sensor configured to capture current ratio regarding the sympathetic activity level and the parasympathetic activity level;
extracting the future profile ratio from a database based on monitored performance of a task over a time-period during the task-performance; training the future profile ratio between the sympathetic activity level and the parasympathetic activity level from the current ratio according to training imparted as part of factory settings or in an offline state based on extracted from the database;
storing, the database, the future profile ratio based on the trained data;
predicting the future profile ratio between the sympathetic activity level and the parasympathetic activity level from the current ratio based on a machine learning model;
continuously-updating and storing in the database the captured future profile ratio including the current ratio between the sympathetic activity level and the parasympathetic activity level using the wearable electronic device;

performing re-training of the machine learning model based on the stored captured future profile ratio including the current ratio between the sympathetic activity level and the parasympathetic activity level; and predicting the change in the ratio based on the re-trained machine learning model.

2. The method according to claim 1, wherein the assignment of task to the person is based on a mapping between:
   a) a complexity associated with the task to be assigned; and
   b) the calculated ratio.

3. The method according to claim 2, wherein the complexity associated with the task is defined by at least one of:
   time-duration required for task-completion;
   probability of failure;
   level of skill set required;
   a magnitude of resources required;
   expected energy consumption; and
   infrastructure requirement.

4. The method of claim 1, wherein the one of the tasks corresponding to the minimum ratio is a task other than rest or break.

5. A system for apportioning tasks to a person in an environment, comprising:
   a processor; and
   a memory storing a program, wherein:
   the program, when executed by the processor, causes the processor to perform:
   calculating, by using a computer, a sympathetic activity level of a sympathetic nerve of a person according to a first frequency component included in heart rate information obtained by a heart rate monitor and a parasympathetic activity level of a parasympathetic nerve of the person according to a second frequency component lower than the first frequency included in the heart rate information;
   calculating a ratio between the sympathetic activity level and the parasympathetic activity level;
   predicting by a machine learning process a change in the ratio within a predetermined time period for the person, wherein in the machine learning process, a machine leaning criteria draws inferences based on a comparison of the ratio with respect to a most-relevant ratio obtained in historical data; and
   allocating one or more tasks for execution by the person within the predetermined time period based on the calculated ratio and the predicted change in the ratio, and the program further causes the processor to perform:
computing a plurality of ratios between the sympathetic activity level and the parasympathetic activity level with respect to tasks exhibited by one or more persons during performance of the at least one task;

computing a minimum ratio out of the plurality of computed ratios and a corresponding one of the tasks; and assigning, by using the computer, the one of the tasks corresponding to the minimum ratio for execution by the person within the predetermined time period, the executed program further causes the processor to perform the machine learning process that comprises:

acquiring a current ratio between the sympathetic activity level and the parasympathetic activity level using a wearable electronic device, wherein the wearable electronic device includes a sensor configured to capture current ratio regarding the sympathetic activity level and the parasympathetic activity level;

extracting the future profile ratio from a database based on monitored performance of a task over a time-period during the task-performance; training the future profile ratio between the sympathetic activity level and the parasympathetic activity level from the current ratio according to training imparted as part of factory settings or in an offline state based on extracted from the database;

storing, the database, the future profile ratio based on the trained data;

predicting the future profile ratio between the sympathetic activity level and the parasympathetic activity level from the current ratio based on a machine learning model;

continuously-updating and storing in the database the captured future profile ratio including the current ratio between the sympathetic activity level and the parasympathetic activity level using the wearable electronic device;

performing re-training of the machine learning model based on the stored captured future profile ratio including the current ratio between the sympathetic activity level and the parasympathetic activity level; and predicting the change in the ratio based on the re-trained machine learning model.

6. The system of claim 5, wherein the one of the tasks corresponding to the minimum ratio is a task other than rest or break.

* * * * *